US011110101B2

(12) United States Patent
Damaj

(10) Patent No.: US 11,110,101 B2
(45) Date of Patent: Sep. 7, 2021

(54) PROSTATE FUNCTION SUPPORT FORMULA

(71) Applicant: Innovus Pharmaceuticals, Inc., San Diego, CA (US)

(72) Inventor: Bassam Damaj, San Diego, CA (US)

(73) Assignee: Innovus Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 16/867,386

(22) Filed: May 5, 2020

(65) Prior Publication Data

US 2020/0261474 A1 Aug. 20, 2020

Related U.S. Application Data

(62) Division of application No. 15/829,797, filed on Dec. 1, 2017, now abandoned.

(51) Int. Cl.
| | |
|---|---|
| *A61K 31/575* | (2006.01) |
| *A61K 33/04* | (2006.01) |
| *A61K 33/34* | (2006.01) |
| *A61K 31/01* | (2006.01) |
| *A61K 31/4415* | (2006.01) |
| *A61K 33/30* | (2006.01) |
| *A61K 36/185* | (2006.01) |
| *A61P 13/08* | (2006.01) |
| *A61P 13/10* | (2006.01) |
| *A61K 9/20* | (2006.01) |
| *A61K 31/191* | (2006.01) |
| *A61K 31/198* | (2006.01) |
| *A61K 31/355* | (2006.01) |
| *A61K 31/375* | (2006.01) |
| *A61K 36/736* | (2006.01) |
| *A61K 36/82* | (2006.01) |
| *A61K 36/889* | (2006.01) |

(52) U.S. Cl.
CPC .......... *A61K 31/575* (2013.01); *A61K 9/2013* (2013.01); *A61K 9/2054* (2013.01); *A61K 9/2095* (2013.01); *A61K 31/01* (2013.01); *A61K 31/191* (2013.01); *A61K 31/198* (2013.01); *A61K 31/355* (2013.01); *A61K 31/375* (2013.01); *A61K 31/4415* (2013.01); *A61K 33/04* (2013.01); *A61K 33/30* (2013.01); *A61K 33/34* (2013.01); *A61K 36/185* (2013.01); *A61K 36/736* (2013.01); *A61K 36/82* (2013.01); *A61K 36/889* (2013.01); *A61P 13/08* (2018.01); *A61P 13/10* (2018.01)

(58) Field of Classification Search
CPC ..... A61K 31/575; A61K 31/198; A61P 73/08; A61P 13/10
See application file for complete search history.

(56) References Cited

U.S. PATENT DOCUMENTS

| | | | |
|---|---|---|---|
| 5,536,506 | A | 7/1996 | Majeed et al. |
| 5,744,161 | A | 4/1998 | Majeed et al. |
| 7,262,192 | B2 | 8/2007 | Bell et al. |
| 9,161,565 | B1 | 10/2015 | Bezzek |
| 2008/0305096 | A1 | 12/2008 | Verdegem et al. |
| 2009/0143433 | A1 | 6/2009 | Hendrix |
| 2016/0106793 | A1 | 4/2016 | Peltier et al. |
| 2018/0325903 | A1 | 11/2018 | Damaj |
| 2019/0167699 | A1 | 6/2019 | Damaj |

FOREIGN PATENT DOCUMENTS

| | | |
|---|---|---|
| EP | 0810868 | 8/2001 |
| EP | 2027857 | 2/2009 |
| WO | WO 2015/048590 | 4/2015 |
| WO | WO 2015/061860 | 5/2015 |

OTHER PUBLICATIONS

"Astragin®," Nuliv Science, 2018, Product Insert, 2 pages [retrieved online from www.nulivscience.com].
"L-Arginine 500mg with Citrulline 250mg," Puritan's Pride, 2013, 3 pages.
"NuLiv Science announces self-affirmed GRAS for AstraGin ingredient," William Reed Business Media LTD, Mar. 25, 2012, last updated Mar. 15, 2017, 2 pages [retrieved online from: www.nutraingredients-usa.com/articles/2012/03/26nuliv-science-announces-self-affirmed-GRAS-for-AstraGin-ingredient].
"Pygeum," Life Extension Magazine, Apr. 2006, 5 pages [retrieved online from: www.lifeextension.com/magazine/2006/4/aas/page-01?p=1].
"RECALMAX," Innovus Pharmaceuticals, Inc., Oct. 2016, Product Insert, 3 pages.
"Saw Palmetto," WebMD, 2018, 4 pages [retrieved online Sep. 27, 2018 from: www.webmd/com/vitamins/ai/ingredientmono-971/saw-palmetto].
"Vesele," Innovus Pharmaceuticals, Inc., Oct. 2016, Product Insert, 3 pages.
Awad "Effect of beta-sitosterol, a plant sterol, on growth, protein phosphatase 2A, and phospholipase D in LLNCaP cells," Nutr. Cancer, 2000, vol. 36, No. 1, pp. 74-78 (abstract only).
Fry et al. "Impact of nitric-oxide-mediated vasodilation and oxidative stress on renal medullary oxygenation: modeling study," Am J Physiol Renal Physiol, 2016, vol. 310, pp. F237-F247.

(Continued)

*Primary Examiner* — Anna Pagonakis
(74) *Attorney, Agent, or Firm* — Sheridan Ross P.C.

(57) ABSTRACT

The invention provides unit dosage forms and methods that are effective to improve prostate function. Such unit dosage forms and methods are useful to decrease bladder discomfort and improve urinary flow in men.

6 Claims, 3 Drawing Sheets

(56) References Cited

OTHER PUBLICATIONS

Garattini "Glutamic Acid, Twenty Years Later," The Journal of Nutrition, Apr. 2000, vol. 130, No. 4, pp. 901S-909S.
Ghasemi-Mobarakeh et al. "Electrospun poly(epsilon-caprolactone)/gelatin nanofibrous scaffolds for nerve tissue engineering," Biomaterials, 2008, vol. 29, pp. 4532-4539.
Manukhina et al. "General Pathology and Pathopysiology. Role of Nitric Oxide in Prevention of Cognitive Disorders in Neurodegenerative Brain Infuries in Rats," Bulletin of Experimental Biology and Medicine, Oct. 2008, vol. 146, No. 4, pp. 391-395.
Mascio et al. "Lycopene as the most efficient biological carotenoid singlet oxygen quencher," Archives of Biochemistry and Biophysics, Nov. 1989, vol. 274, No. 2, pp. 532-538 (Abstract Only).
Mehmood et al. "Black Pepper and Piperine Possess Antidiarrheal Effect Mediated Through Phosphodiesterase Inhibitory and Ca++ Antagonist Pathways," Basic & Clinical Pharmacology & Toxicology, 2014, vol. 115, Suppl. 1, p. 256, Abstract #834.
Morris, Jr. "Arginine Metabolism: Enzymology, Nutrition, and Clinical Significance, Enzymes of Arginine Metabolism," The Journal of Nutrition, Oct. 2004, vol. 134, No. 10, pp. 2743S-3747S.
Mukhtar et al. "Green Tea in Chemoprevention of Cancer," Toxicological Sciences, 1999, vol. 52, Supplement, pp. 111-117.
Perva-Uzunalic et al. "Extraction of active ingredients from green tea (*Camellia sinensis*): Extraction efficiency of major catechins and caffeine," Food Chemistry, 2006, vol. 96, pp. 597-605.
Riehemann et al. "Plant extracts from stinging nettle (*Urtica dioica*), an antirheumatic remedy, inhibit the proinflammatory transcription factor NF-kappaB," FEBS Letters, 1999, vol. 442, pp. 89-94.
Saigal et al. "Microcrystalline Cellulose as a Versatile Excipient in Drug Research," Journal of Young Pharmacists, 2009, vol. 1, No. 1, pp. 6-12.
Simon et al. "Decoding the Substrate Supply to Human Neuronal Nitric Oxide Synthase," PLOSOne, Jul. 2013, vol. 8, No. 7, e67707, 12 pages.
Official Action for U.S. Appl. No. 15/829,797, dated Apr. 23, 2018 9 pages Restriction Requirement.
Official Action for U.S. Appl. No. 15/829,797, dated Oct. 2, 2018 11 pages.
Official Action for U.S. Appl. No. 15/829,797, dated Jan. 22, 2019 12 pages.
Official Action for U.S. Appl. No. 15/829,797, dated Aug. 23, 2019 7 pages.
Official Action for U.S. Appl. No. 15/829,797, dated Feb. 10, 2020 11 pages.

Supplement Facts

Serving Size: 3 Capsules
Servings Per Container: 30

| | Amt Per Serv. | %DV/RDI |
|---|---|---|
| Vitamin E (d-alpha toco. acetate) | 30 IU | 100% |
| Vitamin B-6 (as pyridoxine hydrochloride) | 5 mg | 250% |
| Zinc (Gluconate) | 50 mg | 333% |
| Selenium (amino acid chelate) | 200 mcg | 286% |
| Copper (gluconate) | 750 mcg | 38% |
| Saw Palmetto (40-45% extract) | 300 mg | ** |
| Beta-Sitosterol | 450 mg | ** |
| Pygeum Africanum (herb powder) | 150 mg | ** |
| Red Raspberry Juice Extract | 75 mg | ** |
| Graviola (powder) | 75 mg | ** |
| Green Tea (50% extract) | 75 mg | ** |
| Cat's Claw (powder) | 45 mg | ** |
| Broccoli (4:1 extract) | 30 mg | ** |
| Lycopene | 15 mg | ** |
| Stinging Nettle (herb powder) | 30 mg | ** |
| Maitake Mushroom | 15 mg | ** |
| Reishi Mushroom | 15 mg | ** |
| Shiitake Mushroom | 15 mg | ** |
| Proprietary Blend | 387 mg | ** |

Consisting of: Quercetin, Juniper Berry Powder, Uva Ursi Powder, Buchu Leaf Powder, Magnesium Stearate, Silicon Dioxide, Glutamic Acid, L-Alanine, L-Glycine, Calcium D-Glucarate, Pumpkin Seed Powder, Burdock Root Powder, Cayenne Pepper Powder, Goldenseal Powder, Gravel Root Powder, Marshmallow Root Powder, Parsley Leaf Powder, and White Pond Lily Powder.

**Daily Value not established.

Other Ingredients: Gelatin, Magnesium Stearate, Stearic Acid, and Microcrystalline Cellulose

*Fig. 4*

PROSTATE FUNCTION SUPPORT FORMULA

RELATED APPLICATIONS

This divisional application claims priority to U.S. application Ser. No. 15/829,797 filed on Dec. 1, 2017, the contents of which is herein incorporated by reference in its entirety.

BACKGROUND OF THE INVENTION

The prostate is a gland that is part of the male reproductive system surrounding the urethra at the neck of the bladder. The main function of the prostate is to make a thin fluid (semen) that lubricates the urethra and transports sperm. As men age, the prostate loses its original structure and function which may lead to urinary problems. Common prostate conditions include prostate cancer which ranks second most common cancer in men. One in seven men will be diagnosed with prostate cancer during his lifetime and is the third leading cause of cancer death in men in the USA (American Cancer Soc. 2017). Symptoms of prostate cancer include difficulty urinating, blood in semen, pelvic and bone pain and erectile dysfunction. Treatment includes radiation therapy, hormone therapy, surgery, chemotherapy, and cryosurgery.

Benign Prostatic Hypertrophy (BPH)—Enlarged Prostate is another common prostate condition in men, with a prevalence of 50%-60% amongst men 60 years or older and 90% for men 70 years or older (Roehrborn, C. G. "Benign Prostatic Hyperplasia: An Overview", Reviews in Urology 7, Suppl. 9 (2005) S3-S14). Approximately 14 million men in the United States have symptoms of BPH. Men with symptomatic BPH have a 23% lifetime risk of developing acute urinary retention (AUR) if left untreated (Rosenberg, M. T., et al, "STEP. Simplified Treatment of the Enlarged Prostate", Int. J. Clin. Pract. (2010), 64(4):488-496). Symptoms of BPH include urinary frequency, nocturia, difficulty urinating, and dribbling. Treatment includes alpha blockers, 5-alpha reductase inhibitors, tadalifil, and surgery.

Yet another prostate condition is Prostatitis; the most common urinary tract problem for men younger than age 50 and the third most common urinary tract problem for men older than age 50. Symptoms of prostatitis include painful or difficult urination and pain in the groin, pelvic area or genitals. Treatment includes antibiotics, alpha blockers, and anti-inflammatory agents.

A need exists for safe and effective supplements to treat prostate conditions.

SUMMARY OF THE INVENTION

Applicant has determined that the beneficial effects of the present invention, a Prostate Function Support Formula are surprising and unexpected to support and enhance prostate function.

The present invention is a dietary supplement to provide prostate function support by safely and effectively supporting prostate health, reduce bladder discomfort and improve urinary flow. The present invention is comprised of clinically tested ingredients, including vitamins, minerals, herbs and a proprietary blend of natural ingredients. Drug side effects are not expected since the present invention does not include non-drug ingredients.

In one embodiment the invention provides a unit dosage form suitable for oral administration in a human comprising:

about 300 mg of Saw Palmetto;
about 450 mg of Beta-Sitosterol;
about 150 mg of *Pygeum africanum*;
about 75 mg of Green Tea extract;
about 15 mg of Lycopene; and
about 30 mg of Stinging Nettle.

In one embodiment, the unit dosage form further comprises Vitamin E.

In one embodiment, the unit dosage form further comprises Vitamin B-6

In one embodiment, the unit dosage form further comprises zinc as zinc gluconate.

In one embodiment, the unit dosage form further comprises selenium as amino acid chelate.

In one embodiment, the unit dosage form further comprises copper as copper gluconate.

In one embodiment, the unit dosage form further comprises Quercetin (2-(3,4-dihydroxyphenyl)-3,5,7-trihydroxy-4H-chromen-4-one).

In one embodiment, the unit dosage form further comprises one or more amino acids selected from L-alanine, L-glutamic acid and glycine.

In one embodiment, the unit dosage form further comprises one or more excipients selected from hydroxypropyl methylcellulose, rice concentrate, and silica.

In one embodiment, the unit dosage form further comprises one or more excipients selected from gelatin, magnesium stearate, stearic acid, and microcrystalline cellulose.

In one embodiment, the unit dosage form is formulated as a capsule.

The invention includes a method to improve prostate function in a man in need thereof comprising administering the unit dosage form of the present invention.

Applicant has determined that men taking the unit dosage form of the present invention report improvements in prostate function, including decreased bladder discomfort and improved urinary flow.

BRIEF DESCRIPTION OF THE FIGURES

FIG. 4 shows supplement facts of the present invention.

DETAILED DESCRIPTION

Figure 1:
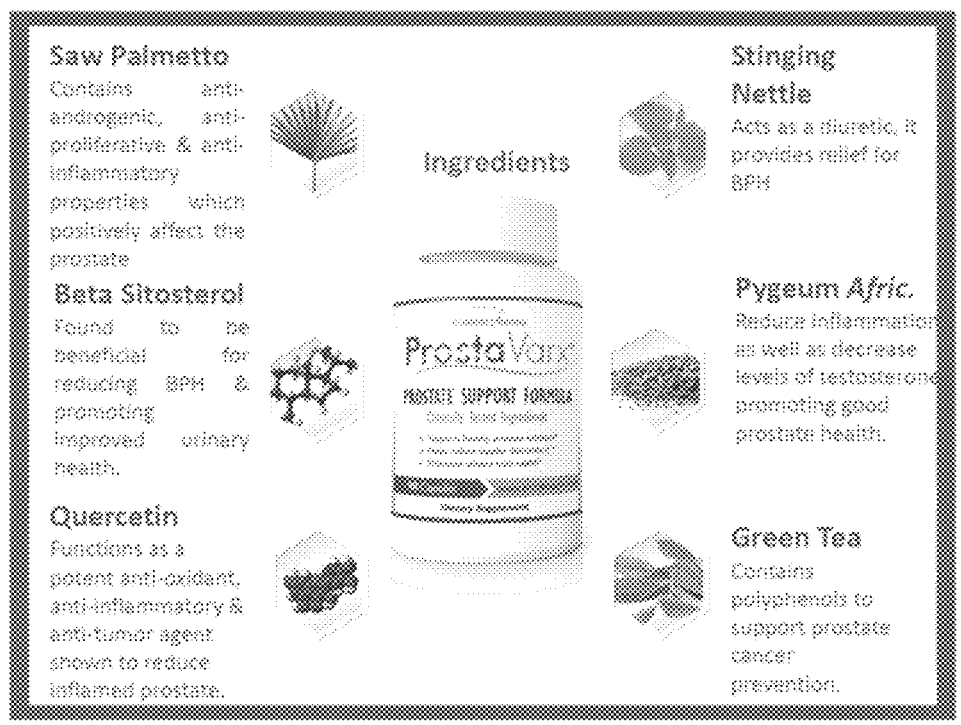
FIG. 1 shows ingredients of the present invention: Saw Palmetto, Beta Sitosterol, Quercetin, Stinging Nettle, *Pygeum africanum*, and Green Tea.
Figure 2:
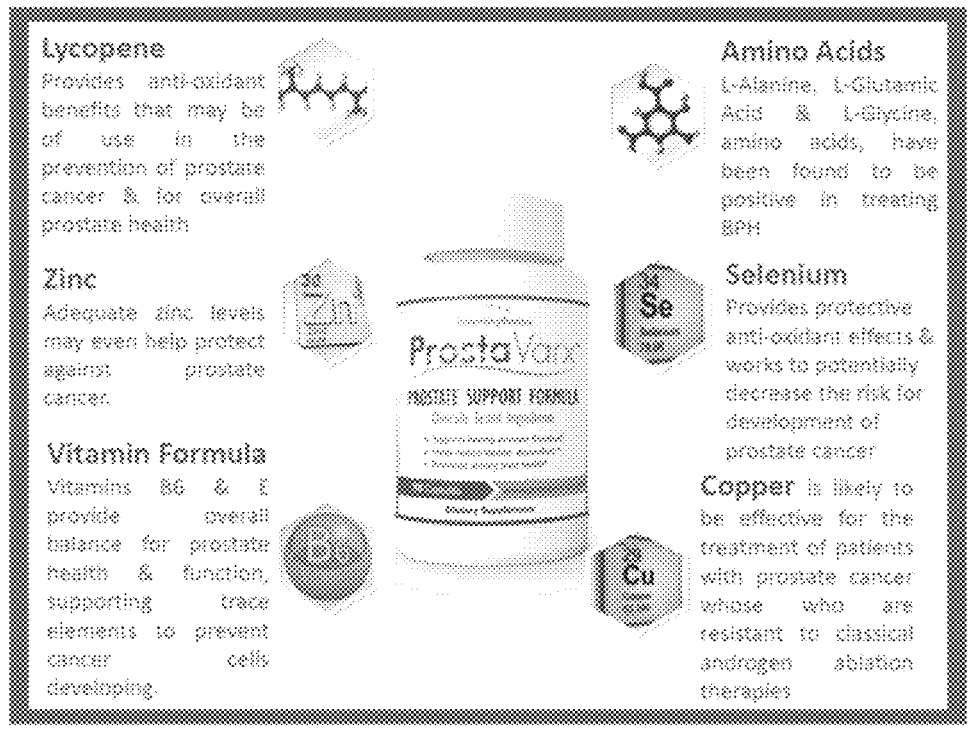
FIG. 2 shows ingredients of the present invention: Lycopene, Zinc, Vitamins B6 and E, Amino Acids, Selenium, and Copper.
Figure 3:
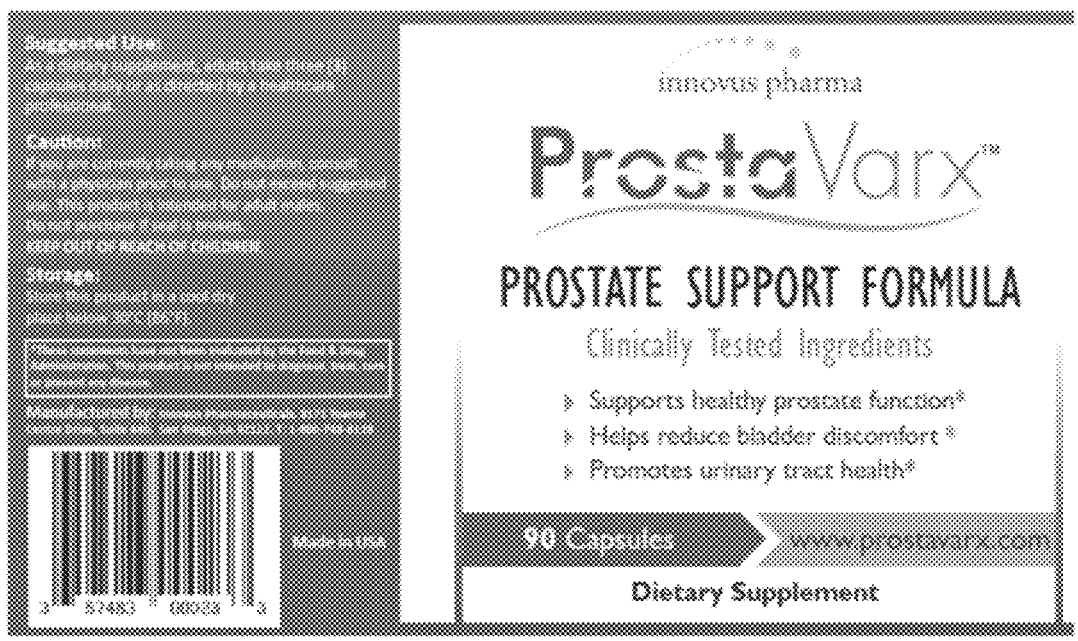
FIG. 3 shows a product label for a composition of the invention.

As used herein, the term "about" has its generally accepted meaning. In one embodiment, the term about means±10% of the associated value. For example, about 100 mg means 100 mg±10 mg. In one embodiment, the term about means±5% of the associated value. For example, about 100 mg means 100 mg±5 mg. In one embodiment, the term about means±2% of the associated value. For example, about 100 mg means 100 mg±2 mg. In one embodiment, the term about means±1% of the associated value. For example, about 100 mg means 100 mg±1 mg.

The present invention is a dietary supplement formulated to support healthy prostate function, reduce bladder discomfort, and promote urinary tract health.

Without limiting to any particular mechanism-of-action, the individual ingredients of the present invention have demonstrated anti-oxidant, anti-inflammatory, chemopreventative, and immunomodulatory properties in in vitro, in vivo, and/or clinical studies. Both individual and combination of the ingredients have bee n clinically studied in prospective, open label, randomized, interventional or observational studies.

The recommended dosage for the present invention is 3 tablets per day dosing regimen by oral administration in men.

In one embodiment, a unit dosage form of the invention may contain one or more pharmaceutical diluents or excipients. For example, in one embodiment a unit dosage form of the invention may comprise microcrystalline cellulose, silicon dioxide, and magnesium stearate. In another embodiment a unit dosage form of the invention comprises one or more excipients selected from hydroxypropyl methylcellulose, rice concentrate, and silica. In another embodiment a unit dosage form of the invention comprises one or more excipients selected from gelatin, magnesium stearate, stearic acid, and microcrystalline cellulose.

The present invention contains Saw Palmetto, a Tier 2 supplement containing fatty acids and beta-sitosterols, commonly used to help men with prostate or urinary symptoms. Saw Palmetto has been shown in vivo (rat) to reduce the weight and inhibit growth of prostate (Talpur, N. et al "Comparison of Saw Palmetto, extract and whole berry, and cernitin on prostate growth in rats", Mol. Cell. Biochem. (2003) 250(1-2):21-26). Saw Palmetto is clinically shown to be comparable or more effective than pharmaceutical drugs for pain and urinary symptoms associated with prostatitis and BPH (Cai, T. et al, Int. J. Antimicrob. Agents (2009) 33(6):549-553; Pais, P. et al, Adv. Ther. (2010) 27(8):555-563; Bondarenko, B. et al, (2003) Phytomedicine). Saw Palmetto may help reduce the pressure that the prostate exerts on the urethra by shrinking the lining of the prostate. Saw Palmetto may reduce cancer cell proliferation and inflammation (Goldmann, W. H. et al, Cell Biol. Int (2001) 25(11):1117-1122; Yang, Y. et al, Intl. Jour. Onc. (2007) 31(3):593-600). Additional clinical studies on Saw Palmettol have shown a statistically significant improvement in urinary symptoms in men with LUTS (Lower urinary tract symptoms), a group of clinical symptoms involving the bladder, urinary sphincter, urethra, and, prostate (Gerber, G. S. et al, Urology (2001) 58960-4, 964-965); progress in CPSI (Chronic Prostitis Symptom Index) scores (Kraychick, S. G. et al, 27th Annual Euro. Assoc. of Urology Cong. Feb. 24-28, 2012, Paris FR), and others (Carraro, J. C. et al, Prostate (1996) 28(4):231-240; Sinescu, I. et al, Urol. Intl. (2011) 86:284-289).

Beta-sitosterols have been shown clinically to decrease levels of DHT (hormone linked to BPH) and significantly improve urinary flow (Berges, R. R. et al, (Lancet (1995) 345:1529-1532; Klipper, K. F. et al, BR J. Urol. (1997) 80(3):427-432). Data comparing men treated with beta-sitosterol to those receiving placebo indicate a significant decrease in symptom scores in the beta-sitosterol group after three and six months of treatment. In a follow-up study, these improvements were maintained for an additional 18 months of observation.

Stinging Nettle is an herb commonly used to treat urinary problems associated with BPH and urinary tract infections (UTI). Stinging Nettle is clinically shown to relieve difficulty in urinating and urge to urinate caused by BPH (Ghorbanibirgani, A. et al, Iran. Red Cres. Med. J. (2013) 15(1):9-10; Pavone, C. D. et al, Yrologia (2010) 77(1):43-51; Safarinejad, M. R. et al, J. Her. Pharmacother. (2005) 5(4):1-11). In vitro, Stinging Nettle is seen to interfere with SHGB and prevent it from combining with androgens (Nahata, A. et al, Andrologia (2012) 44:396-409). Stinging Nettle acts a 5-α-reductase inhibitor, preventing the conversion of testosterone to Dihydrotestosterone (DHT) (Lopatkin, N. et al, World J. Urol. 2005). The German Commission E approves the use of nettle leaf as supportive therapy in patients with LUTS (combined with immune and antimicrobial therapy) and to prevent and treat formation of urinary gravel.

Stinging Nettle leads to significant reduction in IPSS (International Prostate Symptoms Score), serum PSA (prostate specific antigen) and prostate size in a prospective, randomized double blind, placebo controlled cross over clinical trial of 558 men with BPH (Safarinejad, M. R. et al, J. Her. Pharmacother. (2005) 5(4):1-11). In a similar trial of 100 men with BPH, the treatment group had better effects in relieving clinical symptoms in BPH patients compared to placebo (Ghorbanibirgani, A. et al, Iran. Red Cres. Med. J. (2013) 15(1):9-10). In one embodiment the Stinging Nettle is used as a herb powder.

Combination therapy clinical studies of Saw Palmetto with Stinging Nettle or Quercetin reduced the symptoms in 85% of LUTS secondary to BPH patients (Pavone, C. D. et al, Yrologia (2010) 77(1):43-51), showed IPSS improvement (Bondarenko, B. et al, (2003) Phytomedicine), was superior to placebo (Lopatkin, N. et al, World J. Urol. 2005), and relieved symptoms of prostatitis (Cai, T. et al, Intl. J. Antimicrob. Agents (2009) 33(6):549-553).

Quercetin (CAS Reg. No. 117-39-5), named as 2-(3,4-dihydroxyphenyl)-3,5,7-trihydroxy-4H-chromen-4-one, is a plant polyphenol from the flavonoid group, found in many fruits, vegetables, leaves, and grains. Quercetin is a Tier 1 supplement and naturally occurring flavonoid recognized as a potent antioxidant, anti-inflammatory and gives relief of symptoms associated with prostatitis. Quercetin promoted prostate cancer cells apoptosis and caspase activation in vitro (Kim, Y. H. et al, J. Cell. Biochem. (2007) 100(4):998-1009; Lee, D. H. et al, Biochem. Pharmacol. (2008) 75(12): 2345-2355; Xing, N. et al, Carcinogenesis (2001) 22:409-414; Wang, G. et al, Oncol. Rep. (2013) 30:357-363). Quercetin is effective in vivo in combination with finasteride to reduce prostate weight and anti-tumor activity (Ma, Z. et al, J. Endocrinol. (2004) 181(3):493-507; Ferry, D. R. et al, Clin. Cancer Res. (1996) 2(4):659-668). Quercetin is clinically shown to provide symptomatic improvement in CP/CPPS and shown to enhance the efficacy of antibiotic to treat CP when used in combination with other natural ingredients; saw palmetto and stinging nettle (Cai, T. et al, Intl. J. Antimicrob. Agents (2009) 33(6):549-553). Quercetin is a recommended treatment through the UPOINT System for Prostatitis Treatment used by medical professionals (Shoskes, D. A. et al, Urology (2010) 75(6); Shoskes, D. A. et al, Urology (1999) 54(6):960-963) demonstrating decrease in IPSS in a randomized, double-blind, placebo controlled clinical trial. Quercetin has an effect on human prostate tumor in vivo xenografts in mice and inhibits prostate cancer cell proliferation in vitro (Yang, F. et al, Oncology Reports (2016) 35(3):1602-1610).

*Pygeum africanum* is a Tier 2 herb used to promote prostate and bladder health, BPH, and nocturia (also known as nycturia, the need to urinate at night) reduction. The major active components of *Pygeum africanum* are fat-soluble sterols (phytosterols) and fatty acids that can inhibit the production of DHT (dihydrotestosterone), pro-inflammatory prostaglandins in the prostate (Andro, M. C. et al, Curr. Ther. Res. (1995) 56:796-817; Monograph. "*Pygeum africanum*", Alternative Medicine Review. (2002) V7(1)), and triterpenes and ferulic acid nesters to block the accumulation of cholesterol in the prostate. *Pygeum africanum* is shown in vitro and in vivo to modulate bladder contractility, inhibit cancer cell proliferation and viability, promote cell apoptosis, and suppress production of prostaglandins (Levin, R. M. et al, J. Urol. (1996) 156:2084-2088; Santa Maria, M. A., et al, Arch. Esp. Urol. (2003) 56(4):369-378; Boulbes, D. et al, BJU Int. (2006) 98(5):1106-1113; Quiles, M. T. et al, Prostate (2010) 70(10):1044-1053; Papaioannou, M. et al, Invest. New Drugs (2010) 28(6):729-743). *Pygeum Africanum* is clinically shown to improve urinary flow, reduce nocturia, and improve prostate symptoms, urinary parameters, and sexual function in men with BPH or prostatitis (Andro, M. C. et al, Curr. Ther. Res. (1995) 56:796-817; Carani, C. et al, Arch. Ital. Urol. Nefrol. Androl. (1991) 63(3)341-345; Chatelain, C. et al, Urology (1999) 54(3): 473-478; Barlet, A. et al, Wein Klin. Wochesschr. (1990) 102:667-673; Breza, J. et al, Curr. Med. Res. Opin. (1998) 14(3):127-139).

Green Tea Extract is a Tier 2 supplement with antioxidant qualities to provide support for prostate health, normal prostate size, and anti-cancer protective effect. Green Tea Extract is shown to regulate DHT production and hormones that influence prostate volume. Catechins (polyphenol compounds) in green tea shown to have anti-inflammatory qualities, reduce infection, enhance the immune system, and regulate the production and activities of hormones (Alschuler, L. et al, Am. J. Natur. Med. (1996) 5:28-31; Graham, H. N. et al, Prev. Med. (1992) 21:334-350). In vitro, in vivo and clinical studies identified EGCG (green tea catechin) to be a modulator of molecular pathways to prostate carcinogenesis (Nihal, A. et al, Nutr. Rev. (1999) 57:78-83; Ahmad, N. et al J. Natl. Cancer Inst. (1997) 89:1881-1886). In vitro EGCG acts as an anti-androgen antagonist, suppresses prostate cancer cell proliferation and production of prostate-specific antigen (PSA), reduces tumor size and delays development of prostate tumors in TRAMP mice (Adhami, V. M. et al, Clin. Cancer Res. (2009) 15(6):1947-1953; Gupta, S. et al, Proc. Natl. Acad. Sci. USA (2001) 98(18):10350-10355; Kim. S. J. et al, Cancer Prev. Res. (2014) 7(4):435-444). Clinically shown in randomized trials to reduce overall rate of progression of prostate cancer in men with HGPIN (high-grade prostatic intraepithelial neoplasia), an abnormality of prostatic glands and believed to precede the development of prostate adenocarcinoma, the most common form of prostate cancer (Kumar, N. B. et al, Cancer Prev. Res. (Phila) (2015) 8(10):879-887; Bettuzzi, S. et al, Cancer Res. (2006) 66(2):1234-1240; Brausi, M. et al, Eur. Urol. (2008) 54(2):472-473). Other clinical trials with great tea and/or its components shown benefits of decreased PSA levels, and other biomarkers correlated with prostate cancer (Henning, S. M. et al, Prostate (2015) 75(5):550-559; McLarty, J. et al, Cancer Prev. Res. (2009) June 19; Nguyen, M. et al, Cancer Prev. Res. (Phila) (2012) 5(2):290-298).

Lycopene is a Carotenoid produced by plants. Lycopene enhances antioxidant response to support prostate health and is generally recognized as safe (GRAS). Epidemiological/ Clinical studies link increased lycopene consumption with decreased prostate cancer risk, decreasing serum PSA levels, suppression of tumor growth and supporting urinary function (Obermuller-Jevic, U. C. et al, J. Nutr. 133(11):3356-3360; Ford, N. A. et al, Nutr. Cancer (2011) 63(2):256-263; Yang, C. M. et al, J. Nutr. Biochem. (2012) 23(1):8-17; Zhang, X. et al, Chin. Med. J. (2010) 123(16):2231-2236; Mariani, S. et al, Int. J. Mol. Sci. (2014) 15(1):143301440; Qiu, X. et al, Cancer Prev. Res. (Phila) (20-13) 6(5):419-427; Tang, Y. et al, Neoplasia (2011) 13(2):108-119; Gann, P. H. et al, Cancer Res. (1999) 59(6):1225-1230). Animal studies show antitumorigenic effect (Yang, C. M. et al, Mol. Nutr. Food Res. (2011) 55(4):606-612; Yang, C. M. et al, J. Nutr. Biochem. (2012) 23(9):1155-1162). Lycopene is shown in vitro and in vivo to enhance the antioxidant response of prostate cells, inhibit proliferation, demonstrate chemopreventive effect induce apoptosis and decrease the metastatic capacity of prostate cancer cells and may affect insulin-like growth factor (IGF) intracellular pathway in prostate cancer cells (Konijeti, R. et al, Prostate (2010) 70(14):1547-1554; Kim, H J. S. et al, Nutr. Cancer (2003) 47(1):40-47). Clinical trials with lycopene showed reduction of PSA levels (Kucuk, O. et al, Exp. Biol. Med. (2202) 227(10):881-885; Schwarz, S. 1391(1):49-53; Mohanty, N. K. et al, Urol. Oncol. (2005) 23(6):383-385; Ansari, M. S. et al, BJU Intl. (2003) 92(4):375-378).

Vitamin E, an essential vitamin, and Selenium, an essential mineral, have antioxidative properties and are widely used to prevent damage to the cells, tumor suppression in prostate cancer and provide immune support. Vitamin E and selenium have been shown in vitro and in vivo to reduce risk of prostate cancer, suppress tumor progression and cell apoptosis (Pinto, J. T. et al, Int. J. Cancer (2007) 120(7): 1410-1417; Zhang, Y. et al, Proc. Natl. Acad. Sci. USA (2002) 99(11):7408-7413; Limpens, J. et al, J. Nutr. (2006) 136:1287-1293; Malafa, M. et al, Intl. J. of Cancer (2006) 118(10):2441-2447). Selenium has shown in vitro to decrease the activity of the androgen receptor leading to apoptosis and growth inhibition on prostate cancer cells, increase levels of p53 (tumor suppression) and regulate oxidative and the immune system (Kong et al, Biomaterials (2011) 32(27):6515-6522; Sarveswaran, S. et al, Int. J. Oncol. (2010) 36(6):1419-1428). Higher blood selenium concentrations have been clinically associated with decreased prostate cancer (EPIC and Physicians' health study) and decrease PSA levels (Clark, L. C. et al, British J. of Urol. 1998) 81:730-734; Allen, N. E. et al, Am. J. Clin. Nutr. (2008) 88(6):1567-1575; Li, H. et al, J. Natl. Cancer Inst. (2004) 96(9):696-703; Meyer, H. A. et al, Cancer Epidemiol. Biomarkers Prev. (2009) 18(9):2386-2390).

Vitamin B-6 is required for proper prostate function cell repair and immune health, and the proper manufacture and metabolism of hormones necessary for prostate health.

Zinc is a Tier 3 supplement for prostatitis, prostate cancer and BPH. Zinc induces apoptosis and antiproliferative effects on prostate cancer and BPH cells in vitro (Costello, L. C. et al, Open Urol. Nephrol. J. (2008) 1; Franklin, R. B. et al, Arch. Biochem. Biophys. (2007) 463(2):211-217. Zinc plays a role in testosterone, sperm formation and motility, and DNA damage repair (Netter, A. et al, Arch. Androl. (1981) 7(1):69-73). Clinical experience associates an inverse relationship between zinc intake and risk of prostate issues (Medarova, Z. et al, Am. J. Cancer Res. (2014) 4(4):385-393; Costello, L. C. et al, Mol. Cancer. (2006) 5:17; Mahmoud, A. M. et al, PLoS ONE (2016) 11.11 e0165956 PMC).

"Zinc gluconate" is the zinc salt of gluconic acid. It is an ionic compound consisting of two anions of gluconate for each zinc (II) cation. Zinc gluconate is available from a number of commercial sources.

"Selenium as an amino acid chelate" is an enhanced form of selenium, a vital trace element nutrient with multiple roles in the growth and functioning of living cells in higher animals and humans. Inorganic salt forms of selenium such as sodium selenite and sodium selenite when complexed or incorporated with amino acids, such as aspartic acid and methionine, form selenium-amino acid chelates with enhanced absorption properties.

"Copper gluconate" is the copper salt of gluconic acid. It is soluble in water and insoluble in ethanol. Copper gluconate is available from a number of commercial sources.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to improve prostate function in a man in need thereof comprising administering a unit dosage form to the man wherein the unit dosage form consists of the active ingredients:
   300 mg±15 mg of Saw Palmetto;
   450 mg±22.5 mg of Beta-Sitosterol;
   150 mg±7.5 mg of *Pygeum africanum*;
   75 mg±3.75 mg of Green Tea extract
   15 mg±0.75 mg of Lycopene; and
   30 mg±1.5 mg of Stinging Nettle.

2. The method of claim 1 wherein bladder discomfort is decreased.

3. The method of claim 1 wherein the unit dosage form is administered in the form of three capsules or tablets per day.

4. The method of claim 1 wherein the unit dosage form comprises one or more excipients selected from hydroxypropyl methylcellulose, rice concentrate, and silica.

5. The method of claim 1 wherein the unit dosage form comprises one or more excipients selected from gelatin, magnesium stearate, stearic acid, and microcrystalline cellulose.

6. The method of claim 1 wherein the unit dosage form is formulated as a capsule or a tablet.

* * * * *